United States Patent [19]

Verbeek et al.

[11] Patent Number: 5,034,553
[45] Date of Patent: Jul. 23, 1991

[54] PLATINUM-(II-DIAMINE COMPLEX, METHOD FOR THE PREPARATION OF THIS COMPOUND, PREPARATION WITH AN ANTI-TUMOUR ACTION WHICH CONTAINS THIS COMPOUND AND ALSO SHAPED PREPARATIONS WITH AN ANTI-TUMOUR ACTION

[75] Inventors: Francois Verbeek, Hamelen; Harmen A. Meinema, Leusden, both of Netherlands

[73] Assignee: Nederlandse Organisatie Voor Toegepast-Natuurwetenschappelijk Onderzoek, The Hague, Netherlands

[21] Appl. No.: 387,593

[22] Filed: Jul. 31, 1989

[30] Foreign Application Priority Data

Aug. 31, 1988 [NL] Netherlands .......................... 8802150

[51] Int. Cl.$^5$ ...................... C07F 15/00; A61K 31/28
[52] U.S. Cl. ........................................ 556/137; 556/40
[58] Field of Search ................... 556/137, 40; 514/492; 424/464, 617

[56] References Cited

U.S. PATENT DOCUMENTS 4,410,544 10/1983 Berg et al. ............................ 556/137
4,864,043 9/1989 Nowatari et al. ...................... 556/40

FOREIGN PATENT DOCUMENTS 8392115 of 1983 Netherlands .
2024823A of 1979 United Kingdom .
2066819A of 1981 United Kingdom .
2128615A of 1983 United Kingdom .

Primary Examiner—Arthur C. Prescott
Attorney, Agent, or Firm—Bachman & LaPointe

[57] ABSTRACT

The invention relates to a platinum-(II)-diamine complex having the formula set out below:

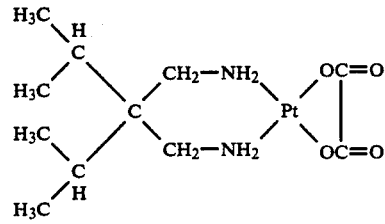

to a method for the preparation of said compound, to a preparation with an antitumour action containing said compound, to shaped preparations with an antitumour action and to shaped preparations with an antitumour containing said compound.

1 Claim, 1 Drawing Sheet

PLATINUM-(II-DIAMINE COMPLEX, METHOD FOR THE PREPARATION OF THIS COMPOUND, PREPARATION WITH AN ANTI-TUMOUR ACTION WHICH CONTAINS THIS COMPOUND AND ALSO SHAPED PREPARATIONS WITH AN ANTI-TUMOUR ACTION

BACKGROUND OF THE INVENTION

Platinum-(II)-diamine complex, method for the preparation of this compound, preparation with an anti-tumour action which contains this compound and also shaped preparations with an anti-tumour action.

The invention relates to a platinum-(II)-diamine complex and also to a method for the preparation of this compound, to a preparation with an anti-tumour action which contains this compound and also to shaped preparations with an anti-tumour action.

About twenty years ago the American biochemist B. Rosenberg discovered that cis-diamine-dichloro-platinum (cis-platinum) exhibits a very strong anti-tumour activity; B. Rosenberg, L. van Camp, J. Trosko and V. H. Mansour, Nature 222, (1969) pages 385–386. In the meantime this compound, in combination with other anti-tumour agents, has found important applications in the treatment of tumours, in particular of the ovary and testes. Cis-platinum has, however, a number of highly undesirable side effects. It causes severe nausea in the patient, in combination with vomiting. In addition, it displays kidney, bone marrow and neurotoxicity and can cause damage to the hearing. Reference is made here, for example, to the article by D. Th. Sleijfer, S. Meijer and M. H. Mulder, Cis-platin: a review of clinical applications and renal toxicity. Pharm. Weekbl. [Sci.] 1985; 7: pages 237–244. Since the start of the 1970s, a great deal of research has also been carried out world-wide on the mechanism of action of cis-platinum and on the development of analogues with a higher anti-tumour activity and/or activity against tumours not susceptible to date, analogues with reduced toxic side effects and/or analogues with improved physical and pharmacological properties.

Numerous platinum-diamine complexes are known from the literature. However, there is still a great need for new anti-tumour agents, specifically for compounds with activity against tumours which are resistant or have developed resistance to cis-platinum.

Reference is made here, for example, to two recent review articles and to the literature references mentioned therein; E. W. Stern, The Search for New Platinum Antitumor Agents: Progress, Problems and Prospects, in Platinum and other Metal Coordination Compounds in Cancer Chemotherapy, Edited by Marino Nicolini, Martinus Nijhoff Publishing, Boston, Dordrecht, Lancaster, ISBN 0-89838-358-7, 1988, pages 519–526; H. A. Meinema, Platinaverbindingen ter bestrijding van kanker: synthese, eigenschappen en structuuractiviteitsrelaties (Platinum compounds for combating cancer: synthesis, characteristics and structure-activity relationships) Pharm. Weekbl., 123 (1988) pages 549–552.

Diamine-platinum complexes are described in Dutch Patent Application No. 79.04740 which are shown in FIG. 1 of the drawing where $R_1$ and $R_2$ independently of one another represent a hydrogen atom or a substituted or unsubstituted alkyl, cycloalkyl, aryl or aralkyl group, while $R_1$ and $R_2$ together with the carbon atom to which they are bonded can be a substituted or unsubstituted cycloalkyl group, $R_3$ and $R_4$ independently of one another represent a hydrogen or a substituted or unsubstituted alkyl, aryl or aralkyl group and X represents an anionic group.

Diamine-platinum complexes are known from Dutch Patent Application 82.04067 as shown in FIG. 1 of the drawing wherein $R_1$ and $R_2$ both represent an ethyl group or, together with the carbon atom to which they are bonded, a phenyl group (it is pointed out here that the examples indicate that it is not a phenyl group but a cycloalkyl group which is meant), $R_3$ and $R_4$ both represent a hydrogen atom and each X represents a chloroacetate or nitrate group, or two symbols X together represent a malonate group, an ethylmalonate group, a hydroxymalonate group, a carboxyphthalate group, a cyclobutane-1,1-dicarboxylate group or an oxylate group, or a sodium salt of one of these groups.

Extensive research carried out by the National Cancer Institute, Bethesda, U.S.A. and the European Organization for Research on the Treatment of Cancer, Brussels, Belgium, has shown that these compounds exhibit a high therapeutic activity against cancer. In comparison with other platinum complexes for combating cancer which are known and are used in practice, these complexes have a lower kidney toxicity.

Platinum complexes with an anti-tumour action are known from Dutch Patent Application 80.00032, now patent 181,434, which has the formula shown in Figure of the drawings, wherein $R_1$ and $R_2$ independently of one another represent a hydrogen atom or a substituted or unsubstituted alkyl, cycloalkyl, aryl or aralkyl group, while $R_1$ and $R_2$, together with the carbon atom to which they are bonded, can form a substituted or unsubstituted cycloalkyl group, $R_3$ and $R_4$ independently of one another represent a hydrogen atom or a substituted or unsubstituted alkyl or aralkyl group and X and Y represent identical or different anionic groups. These compounds also exhibit an action against a number of types of cancer and a reduced kidney toxicity.

SUMMARY OF THE INVENTION

It has now been found that a compound having the formula set out below has a surprisingly good action against strains which have become resistant to cis-diamine-dichloro-platinum (cis-platinum).

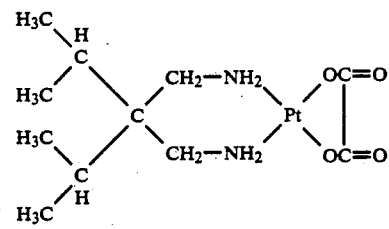

BRIEF DESCRIPTION OF THE DRAWINGS

The present invention will be more clearly understood from a consideration of the attached drawings wherein.

DETAILED DESCRIPTION

Figure 1:
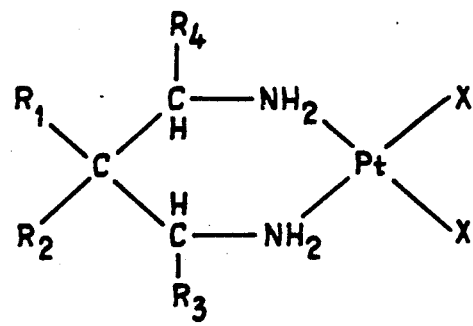
FIGS. 1 and 2 represent prior art compounds.
Figure 2:
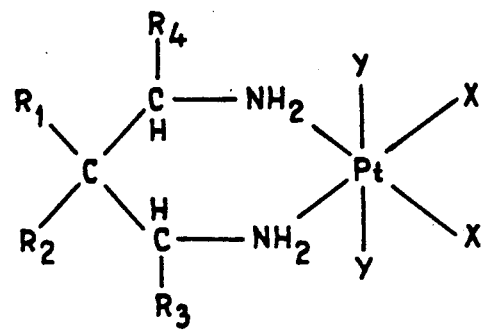
Figure 3:
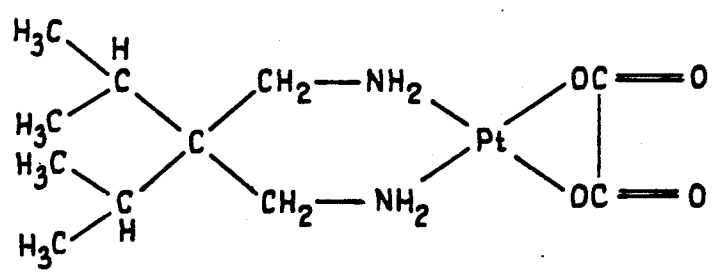
FIG. 3 represents the compound of the present invention and FIG. 4 shows the starting material in the preparation of the compound of the present invention.
Figure 4:
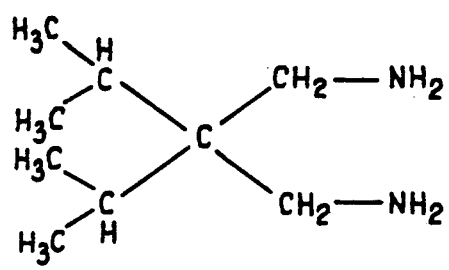

The above compound having the formula shown in Figure (TNO-56) shows a good anti-tumour action against L1210 leukaemia; % T/C is a maximum of 144/20 mg/kg, while in a control experiment cis-platinum reaches a % T/C of at most 138 (6–10 mg/kg). M5076 sarcoma, implanted i.p. and treated i.p. gives a maximum % T/C of 193 (12 mg/kg), while with cis-platinum a maximum % T/C of 166 (4.8 mg/kg) is obtained. M5076 sarcoma, implanted s.c. (subcutaneously) and treated i.v. (intravenously), gives a maximum % T/C of 144 (12 mg/kg), while cis-platinum gives a maximum % T/C of 144 (2.4 mg/kg).

It is particularly interesting that this compound (TNO-56) exhibits a strong cytotoxic action against cell lines (A2780/124 and A2780/DDP) of A2780 human ovary carcinoma which are resistant to cis-platinum. The compound even appears to have a stronger action against cell lines A2780/124 and A2780/DDP, which are resistant to cis-platinum, than against the cell line A2780 which is not resistant to cis-platinum. This is expressed in $IC_{50}$ ratios of, respectively, 0.7 and 0.5 for $IC_{50}$ A2780/124 versus $IC_{50}$ A2780 and $IC_{50}$ A2780/DDP versus $IC_{50}$ A2780.

For cis-platinum itself these values are 10 and 12.6 respectively. A criterion for an interesting action against resistant cell lines is a $IC_{50}$ ratio of $\leq 4.0$.

The active compound obtained can be processed to pharmacological preparations in a manner known per se. The conventional additives can be used here.

The active compound according to the invention can be prepared in a manner known per se. The preparation is illustrated in the following examples.

EXAMPLE IA 2,2-Diisopropyl-1,3-diaminopropane di-HCl salt 4.75 g (0.03 mol) 2,2-diisopropyl-1,3-diaminopropane di-HCl salt are dissolved in 70 ml absolute toluene. The solution is cooled in ice and dry HCl gas is passed through for ½ hour.

The toluene is evaporated off by applying a reduced pressure achieved with a water jet pump. A white solid substance remains: 6.9 g (99%).

'H-NMR spectrum in $D_2O$: (Varian T-60) (shifts in dpm relative to the Na salt of trimethylsilylpropanesulphonic acid)
$CH_2$: 1.00 (d)
$CH_2$: 3.07 (s)
CH: 2.07 (m)
$NH_3^+$: 4.67 (s)

EXAMPLE IB

Cis-dichloro-2,2-diisopropyl-1,3-diaminopropane platinum (II)

6.9 g (0.03 mol) 2,2-diisopropyl-1,3-diaminopropane di-HCl salt and 12.45 g (0.03 mol) $K_2PtCl_4$ are dissolved in 125 ml distilled water.

The solution is warmed to 90°–95° C.

A solution of 2.7 g NaOH in 20 ml of distilled water is added at a rate such that pH: $\leq 7$ (final pH=7.5).

The pale yellow reaction product is filtered off with suction on a Büchner funnel and rinsed with distilled water (100 ml) and with acetone (50 ml).

The product obtained in this way is dried over potassium hydroxide in a dessicator.

The weight of the dried substance is: 9.0 g (70%).

Elemental analysis: Calculated % by weight C: 25.48; H: 5.23; N: 6.60; Found % by weight C: 25.62; H: 5.18; N: 6.17.

'HNMR spectrum in DMSO-d6 (variant T-60) (shifts in ppm relative to TMS)
$CH_3$: 0.83–0.93 (d)
CH: 1.87 (m)
$CH_2$ ($NH_2$): 2.67 (partially under DMSO-d6)
$NH_2$: 5.37 (satellites 4.73 and 5.93)

EXAMPLE IC 2,2-Diisopropyl-1,3-diaminopropaneoxalatoplatinum (II)

3.2 g (0.0076 mol) cis-dichloro-2,2-diisopropyl-1,3-diaminopropane platinum (II) are suspended in 70 ml distilled water. 2.48 g (0.014 mol) silver nitrate are added to the suspension. The mixture is now warmed at 40°–50° C. for 3 hours with the exclusion of light. The AgCl formed is filtered off and rinsed with distilled water (10 ml).

1.55 g (0.0076 mol) potassium oxalate.$2H_2O$ are added to the filtrate while this is still warm.

The mixture is now stirred for 1 hour at room temperature; the product is then placed in a refrigerator.

The solid substance formed is filtered off with suction and rinsed with distilled water (10 ml) cooled in ice and dried over potassium hydroxide in a dessicator. Weight of dry substance: 3.0 g (89%)

Elemental analysis: Calculated % by weight $0.5H_2O$: C: 29.33; H: 5.15; N: 6.22; O: 15.99; Pt: 43.31; Found % by weight: C: 29.38; H: 4.88; N: 6.37; O: 15.81; Pt: 43.80.

Determination of the biological action of the compound prepared above.

In vitro cytotoxicity

The cytotoxic action of the platinum complex was evaluated in vitro in a cell line panel consisting of B16-F10 murine melanoma, HCT-116 human colon carcinoma, A2780 human ovary carcinoma and 2 sub-lines of A2780 which are resistant to cis-platinum, i.e. A2780/124 and A2780/PPD respectively. The B16-F10 cell line was kept in a culture of Eagle's Minimum Essential Medium (MEM) with Earle's salts (Gibco) enriched with 2 mmol L-glutamine, 2.06 mmol sodium pyruvate, insulin (0.26 units/ml), penicillin/streptomycin (10 units/ml and 10 mcg/ml respectively), MEM non-essential amino acids (0.6% by weight Gibco) and 10% foetal bovine serum (Hyclone). The HCT-116 cells were cultured in McCoy's 5A medium (modified Gibco) which was supplemented with 2 mmol L-glutamine, 0.12 mmol L-serine, 0.17 mmol asparagine, 1.5 mmol sodium pyruvate, MEM essential amino acids (0.625%, Gibco), MEM non-essential amino acids (0.67%, Gibco), MEM vitamins (0.6%, Gibco), foetal calf serum (10%, Hyclone) and penicillin/streptomycin (10 units/ml and 10 mcg/ml). The A2780 cell lines are cultured in RPMI medium 1640 (Gibco Laboratories) supplemented with foetal calf serum (10% Hyclone), 2 mmol L-glutamine and penicillin/streptomycin. All cell lines are incubated at 37° C. in an incubator with 5% by volume $CO_2$ with a high atmospheric humidity.

Logarithmically growing cells are harvested by mild trypsinisation and 4,000 cells are added to a microtitre plate with 96 wells (Costar). The plates are incubated for one night in 5% by volume $CO_2$ at 37° C. to allow the cells to adhere to the plate. The cells are then treated with the platinum complex or cis-platinum and incubated for 72 hours. The plates are turned over and shaken to remove the media, pharmacologically active compounds and cells which have become loose. Formalin (10% by weight) in a phosphate-buffered physiological saline solution is added and the cells are fixed for 10 minutes. The fixative is removed and the plates are dried in air, coloured for 15 minutes with 0.0075% by weight crystal violet, washed twice and dried in air. The spot is rendered soluble with 0.2 ml 0.1M acetic acid/ethanol (1:1) and the optical densities are determined with the aid of a Dynatech MR 600 microtitre plate reader. The IC$_{50}$ values (the concentration in mcg/ml which causes 50% inhibition of the cell growth) were calculated with the aid of linear regression analysis of the absorption data.

The results of the in vitro cytotoxicity tests are given in Table A. The compound in question (TNO-56) is cytotoxic for all five cell lines. However, the most important fact is that the sub-lines of A2780 human ovary carcinoma (A2780/124 and A2780/DDP) which are resistant to cis-platinum are not able to withstand the compound in question.

In fact, these cell lines which are resistant to cis-platinum are more susceptible to the compound in question than was the A2780 line itself, as can be seen from the IC$_{50}$ values for the compound in question, which are lower for the resistant sub-lines than for the susceptible line.

Activity against L1210 murine leukaemia

The platinum complex is investigated for anti-tumour action against L1210 murine leukaemia. CDF$_1$ mice with a weight of 20 g were inoculated intraperitoneally with 10$^6$ ascitic cells of L1210 leukaemia. The administration of the active substance was started the day following the intraperitoneal implantation of the tumour. The complex is administered in diverse amounts by intraperitoneal injections. Groups of 6 mice are used for each dose and they are treated with a single dose of the complex on the treatment day. A group of ten control mice treated with a physiological saline solution was included in the experiment. The groups treated with cis-platinum are included as positive comparisons. The mice were weighed before the treatment and again on the fifth or sixth day and the average change in weight is taken as a measure of the toxicity. The animals are assessed daily for mortality and the experiments are ended after 30 days. The tumour activity is determined on the basis of % T/C, which is the ratio of mean survival time of the group treated with the active substance relative to the mean survival time of the comparison group treated with a physiological saline solution times 100. The mice treated with physiological saline solution usually have a mean survival time of 7 days. A compound is regarded as active when this gives a % T/C≧125%.

Table B contains a summary of the assessment of the complex for the anti-tumour action against L1210 murine leukaemia. The % T/C values which are obtained for each dose examined are indicated. The compound in question (TNO-56) is active at 10 and 20 mg/kg, the maximum T/C being 144% at a dose of 20 mg/kg.

Action against M5076 reticulum cell sarcoma

The complex was also assessed for anti-tumour action against M5076 sarcoma. BDF$_1$ mice, 8 per group, were inoculated intraperitoneally with 10$^6$ cells of M5076 or subcutaneously with a fragment of a M5076 tumour. Mice with an intraperitoneal tumour were treated intraperitoneally starting 13 days after the implantation and this was continued on days 17, 21 and 25, resulting in 4 treatments in all. Mice with an implanted subcutaneous tumour were treated intravenously starting 5 days after the implantation and again on days 9, 13 and 17. Therefore a total of four treatments. Four doses of the complex were tested. A comparison group treated with physiological saline solution and groups treated with cs-platinum are included in this experiment. The mice were assessed daily for survival and the tests were ended after 75 to 80 days. The anti-tumour action was determined on the basis of a) mean survival time of the mice treated with the active substance relative to that of the untreated mice (% T/C) and b) the mean time for subcutaneously implanted tumours to reach a weight of 1 gram in mice treated with active substance relative to the untreated mice (T-C). A compound is regarded as active if this gives a T/C≧125% or is T-C≧13 days.

The results of the tests with the platinum complex are summarized in Table C in which the percentage T/C and T-C which is achieved with each dose tested are indicated.

The compound in question is active against intraperitoneally administered M5076 in all doses tested, a maximum % T/C of 193% being achieved with 12 mg/kg per injection. Against subcutaneously administered M5076, the compound in question causes a dosage-dependent increase in % T/C and tumour inhibition with a maximum response at 12 mg/kg per injection (T/C=144%; T-C=26.8 days).

TABLE A

| | In vitro cytotoxicity | | | | |
|---|---|---|---|---|---|
| | IC$_{50}$ (mcg/ml) | | | | |
| Compound | B16-F10 | HCT116 | A2780 | A2780/124 (ratio)$^a$ | A2780/DDP (ratio)$^a$ |
| Cis-platinum | 9.8 | 8.5 | 2.3 | 23 (10) | 28 (12.6) |
| TNO-56 | 43 | 115 | 221 | 155 (0.7) | 110 (0.5) |

$^a$Ratio = $\frac{\text{IC}_{50}\ \text{A2780/124}}{\text{IC}_{50}\ \text{A2780}}$ or $\frac{\text{IC}_{50}\ \text{A2780/DDP}}{\text{IC}_{50}\ \text{A2780}}$

TABLE B

| Inhibition of L1210 murine leukaemia | | |
|---|---|---|
| Compound | Dose$^a$ | % T/C |
| Cis-platinum | 4 | 131 |
| | 6 | 138 |
| | 8 | 131 |
| | 10 | 138 |
| TNO-56 | 10 | 125 |
| | 20 | 144 |
| | 40 | 88 |

$^a$Dose is mg/kg administered i.p., once on day 1.

TABLE C

| Inhibition of M5076 Sarcoma | | | | |
|---|---|---|---|---|
| Compound | Treatment route | Dose$^a$ | % T/C | T-C (days) |
| A. intraperitoneal implantation | | | | |
| Cis-platinum | ip | 2.4 | 164 | — |
| | | 3.6 | 143 | — |
| | | 4.8 | 166 | — |
| TNO-56 | ip | 4 | 139 | — |
| | | 6 | 154 | — |
| | | 8 | 161 | — |
| | | 12 | 193 | — |
| B. subcutaneous implantation | | | | |
| Cis-platinum | iv | 2.4 | 144 | 23.3 |
| | | 3.6 | 136 | 25.3 |
| | | 4.8 | 141 | 31.8 |
| TNO-56 | iv | 4 | 119 | 7.8 |
| | | 6 | 135 | 14.0 |

TABLE C-continued

| | Inhibition of M5076 Sarcoma | | | |
|---|---|---|---|---|
| Compound | Treatment route | Dose[a] | % T/C | T-C (days) |
| | | 8 | 140 | 21.5 |
| | | 12 | 144 | 26.8 |

[a]Dose is mg/kg administered i.p. on days 13, 17, 21 and 25 to mice with intraperitoneal tumours and administered i.v. on days 5, 9, 13 and 17 to mice with subcutaneous tumours.

What is claimed is:

1. Platinum-(II)-diamine complex having the following formula:

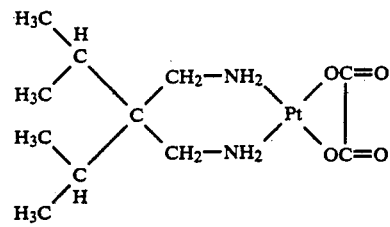

wherein said complex exhibits cytotoxic action against cell lines of human ovary carcinoma which are resistant to cis-diamine-dichloroplatinum.

* * * * *